US00PP35677P2

(12) United States Plant Patent
Kallsen et al.

(10) Patent No.: US PP35,677 P2
(45) Date of Patent: Mar. 12, 2024

(54) MALE PISTACHIO TREE NAMED 'UC WESTSIDE'

(50) Latin Name: ***Pistacia vera* L.**
Varietal Denomination: UC Westside

(71) Applicant: The Regents of the University of California, Oakland, CA (US)

(72) Inventors: Craig E. Kallsen, Bakersfield, CA (US); Dan E. Parfitt, Davis, CA (US)

(73) Assignee: The Regents of the University of California, Oakland, CA (US)

( * ) Notice: Subject to any disclaimer, the term of this patent is extended or adjusted under 35 U.S.C. 154(b) by 0 days.

(21) Appl. No.: 17/803,955

(22) Filed: Feb. 3, 2023

(51) Int. Cl.
*A01H 5/00* (2018.01)
*A01H 6/00* (2018.01)

(52) U.S. Cl.
USPC ..... Plt./152

(58) Field of Classification Search
USPC ..... Plt./152
See application file for complete search history.

(56) References Cited

U.S. PATENT DOCUMENTS

PP17,158 P3 10/2006 Parfitt et al.
PP18,262 P3 * 12/2007 Parfitt ..... A01H 5/08 Plt./152
PP28,994 P3 2/2018 Kallsen et al.

OTHER PUBLICATIONS

Kallsen et al., "'Famoso', a New Male Pistachio Cultivar to Replace 'Peters'," HortScience, Dec. 2017, vol. 52, No. 12, pp. 1829-1831.
Kallsen et al., "UC pistachio cultivars show improved nut quality and are ready for harvest earlier than 'Kerman'," California Agriculture, Apr.-Jun. 2020, vol. 74, No. 2, pp. 86-93.

* cited by examiner

*Primary Examiner* — Susan McCormick Ewoldt
(74) *Attorney, Agent, or Firm* — McKee, Voorhees & Sease, PLC

(57) ABSTRACT

A new male pistachio cultivar (*Pistacia vera* L.) designated as 'UC Westside', to be used advantageously as a pollenizer for commercial female pistachio varieties. 'UC Westside' blooms later in the spring than most existing male pistachio cultivars and is particularly characterized by a reduced juvenility period, dense blooms in years with low chill, good pollen viability, and improved bloom synchrony with standard female pistachio varieties, especially 'Kerman'. It may be used as a replacement for the male cultivar 'Peters'.

6 Drawing Sheets

Botanical designation:
Genus and species: *Pistacia vera* L.
Variety denomination: The new plant has the varietal denomination of 'UC Westside'.

BACKGROUND

Pistachios are dioecious, meaning that to produce nuts, female pistachio trees must be pollenized by a male tree. Fall and winter chilling in California is often suboptimal for a vigorous and synchronous male and female bloom and is predicted to become even more limiting. In any given year, fall and winter chilling may vary from excellent to poor, with marginally adequate being the norm. Under these conditions, identification of a single male cultivar to synchronize bloom with a given female under a range of chilling scenarios is not feasible and more than one male cultivar is required.

Under California conditions, both 'Famoso' (U.S. Plant Pat. No. 28,994) and 'Peters' (not patented) are common pollenizers for the female cultivar 'Kerman' (not patented). 'Famoso' under low to moderate chilling conditions blooms synchronously with 'Kerman', but new research suggests that under adequate or high chilling conditions, 'Famoso' may be at full bloom a few days before 'Kerman'. Similarly, 'Peters' continues to demonstrate some undesirable characteristics. 'Peters' is slower to produce inflorescences as it moves from the juvenile stage to the reproductive stage than is 'Kerman'. 'Kerman' begins to produce numerous inflorescences when it is four years old, but a 'Peters' tree typically has no inflorescences in its fourth year and few in its fifth year. Additionally, under low or moderate chill, which has been common in recent years, 'Peters' has demonstrated irregular and non-synchronous bloom with 'Kerman'. 'Peters' has a long bloom period; however, in years of low or moderate chill, the bloom period can be quite late for 'Kerman' pollenization. In many orchards, the bloom period largely or entirely missed the 'Kerman' bloom period in the 2014 and 2015 low-chill crop years.

Thus, there exists a need for improved male pistachio varieties having a reduced juvenility period and better bloom synchrony with 'Kerman' under all winter chilling scenarios than the present industry standards.

BRIEF SUMMARY

This disclosure relates to a new and distinct male pistachio cultivar (*Pistacia vera* L.) which has been denominated as 'UC Westside'. 'UC Westside' blooms later in the spring than most existing male pistachio trees and has a reduced juvenility period, often producing inflorescences in Year 3 and a dense bloom in Years 4 and 5. The flowering period of 'UC Westside' has been coincident with female pistachio 'Kerman' in years with moderate to high chill and has produced a dense bloom in years of low chill, which overlaps the later bloom period of 'Kerman'. Thus, 'UC Westside' is proposed to augment 'Famoso' and replace 'Peters' in 'Kerman' pistachio plantings. 'UC Westside' has been asexually reproduced by budding near Delano and Famoso in Kern County, California, and near Five Points in Fresno County, California. 'UC Westside' is stable and produces true to type in successive generations of asexual reproduction.

DETAILED BOTANICAL DESCRIPTION

Figure 1:
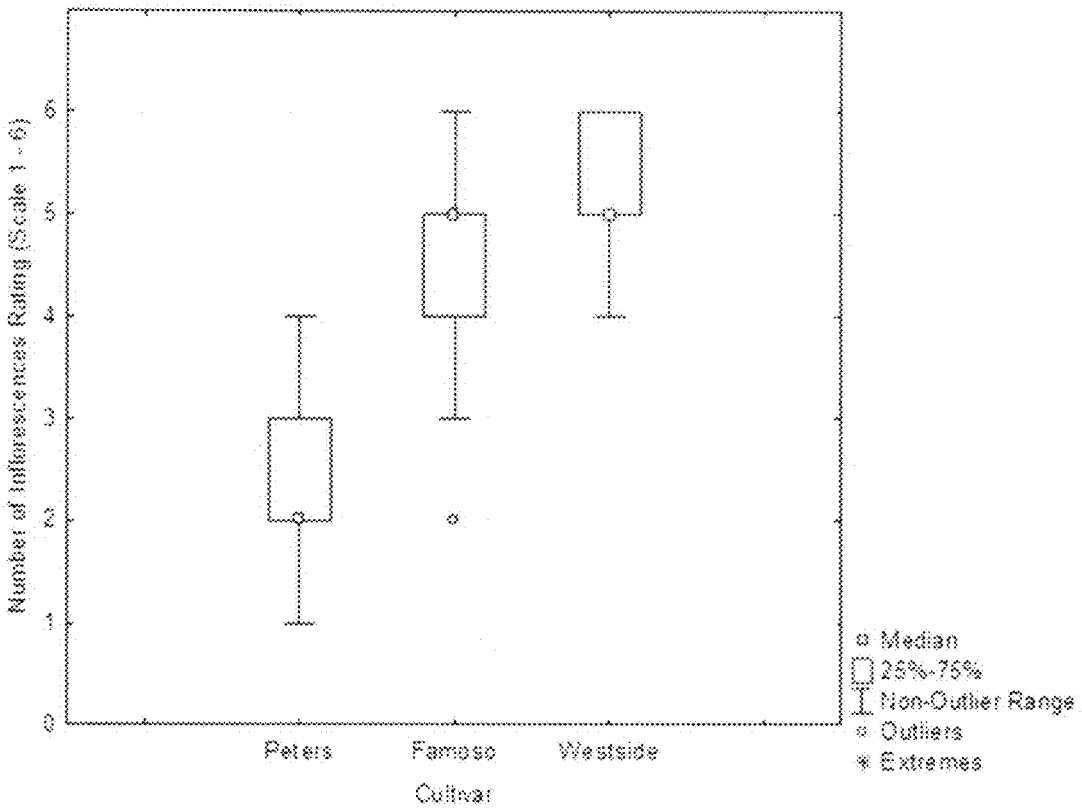
FIG. 1 is a graph depicting the numerical rating for the number of inflorescences of 'UC Westside', 'Famoso', and 'Peters' averaged over four trial locations, 2018-2021. A higher number denotes more inflorescences per tree.

The following is a detailed botanical description of the new variety of 'UC Westside', including the key differentiating characteristics of this variety and comparisons of certain characteristics of 'UC Westside' to other pistachio varieties, as based on observations of various aged specimens grown in several locations in California. Unless otherwise indicated, evaluation data was taken from 3- to 8-year-old trees. Color descriptions are based on the color standards presented in R.H.S. Colour Chart of The Royal Horticultural Society of London (R.H.S.) (1st edition, 1966).

Origin and Selection

'UC Westside' is a hybrid resulting from a cross between 'S-51' (not patented) and an unknown male. It was selected from a seedling evaluation trial located near Five Points, California in the Central Valley. All of the female parents that produced the progeny grown in this trial, and most of the neighboring male pollenizers, demonstrated a reduced juvenility period compared to 'Peters'. 'UC Westside', originally identified as West6-32 in the trial, is the cloned progeny of an open pollinated cross identified as Ao. Ao is a cross between a *Pistacia vera* female 'S-51', which was one of the seedlings (i.e. on its own roots) in a seedling-selection trial established in Bakersfield, California during April 2001, and an unknown male, assumed to be one of the male seedlings in this trial. 'S-51' was selected as a parent because of its reduced juvenility period (i.e. in terms of years to flowering) of the trees in this trial.

The seed that produced West6-32 was collected from 'S-51' in late summer of 2007, germinated in a greenhouse during the winter of 2007-2008 and planted in the field near Five Points, California, 0.9 m (3 ft.) apart with 783 other seedlings in February of 2008. At this trial, only two trees bloomed in 2011 (both males). In 2012, 136 of the original 784 male and female seedlings (17.3%) had at least one open inflorescence (84.6% of which were males). Many of these had few inflorescences. Most of the male trees bloomed too early in the season to be possible pollenizers for 'Kerman'. Nine male selections, including 'UC Westside' were made from this seedling trial after the low-chill winter of 2013-14 and confirmed in the even lower-chill winter of 2014-15. Selection criteria included their juvenility period, bloom density, and apparent synchronization with 'Kerman'. 'UC Westside' and eight other selections were evaluated in three grafted, advanced selection trials in the San Joaquin Valley of California. The three advanced selection trials were called "Whisler", "Corcoran" and "Westside REC". The Whisler trial was further evaluated in two sub-plots at the trial based on difference in altitude (climate) giving a total of four locations. The nine selections in these trials were compared to the male cultivars 'Peters' and 'Famoso' and the female cultivar 'Kerman'.

'UC Westside' was selected as the single best selection based on data collected from 2014 through 2021 for reduced juvenility period, bloom synchrony with 'Kerman', inflorescence density per branch, pollen weight per flower, pollen germination performance and tree size.

Trial Descriptions and Establishment

Nine advanced selections, including 'UC Westside', were made from the Westside REC seedling trial after bloom in 2014 for inclusion in the Whisler trial. The Whisler trial was located near Famoso, California in the Southern San Joaquin Valley within a 'Kerman' orchard, where these male pollenizers were evaluated for juvenility period, bloom density, and apparent synchronization with 'Kerman'. The Whisler trial, ranging from 500 ft.-600 ft. (152-183 m) above sea level, was grafted to PG1 rootstock in August of 2014. This trial consisted of "lower" and "higher" elevation areas. Elevation as used here is a relative term, comprising ca 30.5 m (100 ft.) difference, but resulting in significant differences in chilling because of strong atmospheric inversion layers that form in the San Joaquin Valley during the winter. In this orchard, the pollenizer (i.e. male-containing) rows transversed the orchard perpendicularly to the elevation change. Four rows of 'Kerman' separated each pollenizer row and each pollenizer position within these rows was separated by four 'Kerman' trees. The nine experimental advanced selections plus the cultivars 'Peters' and 'Famoso' were planted in 11 of these pollenizer rows, one each in a pollenizer position in the high elevation area and one in a pollenizer position in the low elevation area of a row.

Bloom characteristics were evaluated again at the Westside REC seedling trial near Five Points, California on the west side of the San Joaquin Valley in spring 2015 following another fall and winter characterized as being very low chill. These same nine males performed well and were included in the Corcoran trial planted in 2015. The Corcoran trial was located near the town of Delano, California on the east side of the San Joaquin Valley within a large 'Kerman' orchard. The Corcoran trial had flat topography and was 63.4 m (208 ft.) above sea level. It was grafted in late July 2015 to clonally propagated 'UCB-1' (not patented) rootstock. The experimental trees were planted in a single male row (every 5th tree) that crossed the orchard. The trial was a randomized, complete block design with three replications of each of the nine advanced selections plus 'Peters' and 'Famoso' (one replication of each selection/cultivar in each block).

Most of these advanced selections, including 'UC Westside' were grafted with replication at the Westside REC advanced female cultivar-selection trial in Five Points, CA in 2015. The Westside REC trial, had flat topography, and was 68 m (223 ft.) above sea level. The trial was grafted in July 2015 on 'UCB-1' seedling rootstocks. Pollenizers were planted in a completely randomized design around the border of the trial, with an additional male row running through the center of the trial. The trial had two 'UC Westside' and three 'Peters' and 'Famoso' trees, which provided the trial data at this location.

Evaluation of Selections

Bloom Evaluation: Bloom was evaluated at specific intervals during the bloom period based on the range of flower development present in individual inflorescences on a given evaluation date (referred to as "range of bloom"). "Mean bloom" was then estimated from the range of bloom present on a given evaluation date. Both of these values, "range of bloom" and "mean bloom" appear in Tables 1-5. The following ratings were used to estimate development of individual inflorescences: 0=dormant bud, 1=green tip (inflorescence bud just starting to swell and push), 2=early bloom (first pollen dehisced for male; first stigmas apparent for 'Kerman'), 3=mid bloom (i.e. about one-half of the estimated maximum number of flowers in an inflorescence that will ever be open are open), 4=full bloom (estimated maximum number of flowers that will ever be open in an inflorescence are open), 5=late bloom (some flowers within the inflorescence are still dehiscing pollen or have fresh stigmas), 6=no flowers dehiscing pollen.

The ratings for evaluating the "mean bloom" of the tree at a given point in time were defined as follows: 0=majority of inflorescence buds on the tree are dormant, 1=majority of the buds on the tree are green tip (bud just starting to swell and push), 2=majority of the inflorescences on the tree are at early bloom (first pollen dehisced for male; first stigmas apparent for 'Kerman'), 3=majority of the inflorescences on the tree are at mid bloom, 4=15 majority of the inflorescences on the tree are at full bloom, 5=majority of the inflorescences on the tree are at late bloom, 6=bloom is done.

In addition, bloom was evaluated for "number of inflorescences" on the tree. This rating system used the following evaluation abbreviations: 1=none, 2=very few (VF), 3=few (F), 4=moderate (M), 5=high (H), 6=very high (VH). Each abbreviation either refers to a range of actual inflorescence numbers on the tree, or as the trees became more mature, to a relative rating comparing inflorescence numbers in a holistic way to the trees in the trial with the greatest number of inflorescences. The method of comparison used is given in the respective table for each year of the trial.

Measurement Of Pollen Germination And Quantity: The date of pollen sampling at three sites was based on the bloom timing of 'Kerman' at each trial site. At the Corcoran trial, branches 30 to 45 cm (1-1.5 ft.) in length with developmentally advanced inflorescences and mostly unopened flowers were collected from each replicated tree of 'Peters', 'Famoso' and 'UC Westside' in the three blocks on the morning of 7 Apr. 2021. At the Whisler trial, on 12 Apr. 2021, branches were collected from 'Peters', 'Famoso' and 'UC Westside' in the 'lower elevation' location and only from 'Peters' and 'UC Westside' in the 'higher elevation' location since 'Famoso' was not present in this plot. In 2021, tree bloom at the Whisler trial was behind that at the Corcoran trial.

The branches collected from both locations from all of the available trees at each location were placed on butcher-block paper in mid-afternoon the same day that they were collected from the field. At 2 p.m. the following day, pollen from the actively dehiscing inflorescences was collected from the butcher-block paper, cleaned of debris and insects with a 145-mesh screen and weighed. Pollen quantity is presented as dehisced pollen per inflorescence. Pollen weights were normalized by division with the number of actively dehiscing inflorescences in each group. Pollen germination is temperature dependent. Temperature in the laboratory was approximately 21.7° C. Beginning at 4 PM and ending at 5 PM, pollen from each cultivar (three replicates at the Corcoran trial and two from the Whisler trial) were germinated on separate hanging drop glass slides. The germination medium was an 18% sucrose solution containing a trace of calcium nitrate and borate. Early the following morning, germinated pollen in the two wells on each slide were counted separately, in three locations within each well, using a microscope (40× objective). These three counts were averaged for each well and germination percentages calculated separately for each of the two wells in the slide. For the Corcoran trial, the average of the two wells was used as the experimental unit in ANOVA (one slide per replicated tree) to determine possible differences among the cultivars and 'UC Westside' for pollen germination. Similarly, the mean weight of pollen per inflorescence was used to determine possible differences among the cultivars and 'UC Westside' for this character. Due to the lack of replication at the Whisler trial, the values obtained, both for "germination percentage" and "weight of pollen per inflorescence" are observational only, from a single tree, but the values presented for germination percentage were averaged from the slides as was done with the Corcoran trial data.

Statistical analyses. Data were analyzed using an ANOVA general linear model statistical package. Bloom timing and number of inflorescences were analyzed by cultivar, location, and year for main effects. Location and cultivar were treated as fixed and year as random variables.

Trial Results and Comparative Analysis

Inflorescence numbers were higher across the trials for 'UC Westside' compared with 'Peters' at the four locations from 2018 through 2021 (Table 1 and FIG. 1). Depending on year and location 'Peters' inflorescence numbers in the individual trials ranged from very few (VF) to moderate (M) while those of 'UC Westside' ranged from M to very high (VH) (Tables 2-4). Limited available data from 2019 and 2020 from the Westside REC trial were included to demonstrate the higher bloom numbers of 'UC Westside' compared to 'Peters', based on observed flower buds that had not yet opened (Table 3). However, this limited data prevented inclusion of the Westside REC data in the bloom timing analysis. In general, 'Peters' lack of inflorescences and the range of maturity of those inflorescences on a given tree made evaluation of bloom timing less precise for this cultivar (Tables 2-4).

Both 'Peters' and 'UC Westside' had a wide range of bloom maturity on the tree during their respective bloom periods (Tables 2-4). Across the trials, mean bloom synchrony with 'Kerman' was not different between 'Peters' and 'UC Westside' at the four locations from 2018 through 2021, although both of these cultivars were later than 'Famoso' (Table 5 and FIG. 2). However, in some years, 'Peters' demonstrated poor synchrony with 'Kerman'. For example, at the Corcoran trial, 'Peters' was in very early bloom (bloom rating ca 2.5) in 2019 and 2021, when 'Kerman' was at or past full bloom with maturity ratings greater than 4.1 (Table 3). It is not clear why the bloom period of 'Peters' was so far behind that of 'Kerman', but this lack of synchrony between the two has been a general concern of the industry for some time in many commercial plantings. This lack of synchrony has been more apparent in very low chill years, which did not occur during this study period. The very low chill winters of 2013-14 and 2014-15, in part, instigated the search for male pollenizers less susceptible to chill.

The bloom synchrony for 'Peters' with 'Kerman' was better at the Whisler trial site (Table 2), but the inflorescence number for 'Peters' was low at this location compared to 'UC Westside', both at the higher and lower elevation locations (Table 1). At all locations 'Famoso' was earlier than both 'UC Westside' and 'Peters'. The earlier bloom of 'Famoso' supports the existing recommendation that 'Kerman' orchards include 'Famoso' as the "early" pollenizer for 'Kerman', especially in low-chill environments.

'UC Westside' demonstrated equal or better pollen germination than did 'Peters' or 'Famoso' at the Whisler and Corcoran trial sites (Table 4). The bloom period was highly extended at the Whisler trial in 2021, probably due to its generally high elevation and borderline chilling. This extended bloom period made scheduling pollen collection challenging due to the difference in bloom timing for 'Kerman' between the higher and lower elevation plots. Based on the advancement of 'Kerman' bloom, pollen was collected at this site on 7 April and 12 April, and at both of these collection dates, very few 'Peters' flowers were close to dehiscing pollen and, in general, there were few flowers to choose from. The only inflorescences ready for collection on 7 April were for 'Famoso' because it was ahead of both 'Peters' and 'UC Westside'. However, 'Famoso' branches with dehiscing inflorescences were collected, again, along with those of 'Peters' and 'UC Westside' on 12 April. On the 7 April collection date, 'Famoso' inflorescence development was not very far along, and by 12 April, most flowers were already open, which limited the ability to collect inflorescences at the right stage for maximum pollen collection in the lab. More 'pollen per inflorescence' was collected from 'Famoso', on average, on 7 April, compared to 12 April, and pollen germination was similar between the two dates (Table 4). 'UC Westside', on 12 April, had a range of inflorescences at a more optimal stage for pollen collection.

At the Corcoran trial site, on 7 April, 'Kerman' was at full bloom, but 'Peters' bloom was later than 'Kerman' bloom, with fewer inflorescences of any stage present and most flowers were immature and unopened (Table 2). The relatively poor germination test results for 'Peters' pollen may have been due to collection of immature inflorescences (Table 4). At the Corcoran site, 'UC Westside' had a similar pollen germination percentage compared to 'Famoso' and a higher germination percentage than did 'Peters' (Table 4). In addition, 'UC Westside' at the Corcoran trial, had significantly more pollen per flower on 7 April, than did 'Famoso' or 'Peters' (Table 4). 'UC Westside' is a superior candidate due to its reduced juvenility period, bloom density, and bloom synchrony with 'Kerman'. Pollen germination across cultivars was, in general, >50% (except for 'Peters') which is sufficient to ensure good pollination, even in the unusually warm bloom period in 2021.

TABLE 1

Summary statistics for differences in number of inflorescences per tree among the male pollenizers ('Famoso', 'Peters' and 'UC Westside') at four locations (UC Westside REC, Whisler Low, Whisler High and Corcoran) for 4 years (2018-2021).

General linear model: Transformed values [Square root (X + 0.5)] versus Location, Year and Cultivar

| Factor | Type | Levels |
|---|---|---|
| Location | Fixed | 4 |
| Year | Random | 4 |
| Cultivar | Fixed | 3 |

Analysis of Variance

| Source | DF | F value | P |
|---|---|---|---|
| Location | 3 | 2.230 | 0.104 |
| Year | 3 | 1.966 | 0.139 |
| Cultivar | 2 | 30.244 | 0.000 |
| Error | 32 | | |
| Total | 40 | | |

Differences in the number-of-inflorescence ratings among 'Peters', 'Famoso' and 'UC Westside'. A larger value denotes more male inflorescences per tree.

| Cultivar | |
|---|---|
| 'Peters' | 2.6 a[Z] |
| 'Famoso' | 4.7 b |
| 'UC Westside' | 5.2 b |

[Z]values in the same column followed with different letters denote significant differences between means using Tuckey's highest significant difference test at P ≤ 0.05

TABLE 2

Bloom characteristics of 4- to 7-year-old 'Kerman', 'Peters', 'Famoso', and 'UC Westside' trees at the Whisler trial, 2018-2021. Trees planted in 2014.

| | Low Elevation Plot [Z] | | | High Elevation Plot | | |
|---|---|---|---|---|---|---|
| Date evaluated | Bloom range [Y] | Mean bloom [Y] | Inflorescence no. [X] | Bloom range [Y] | Mean bloom [Y] | Inflorescence no. [X] |
| Apr. 18, 2018 | | | | | | |
| 'Kerman' | 0.0-3.0[W] | 1.3 | F | 0.0-1.8 | 0.5 | F[W] |
| 'Peters' | 0.0-1.5 | 0.3 | VF | 0.0-1.2 | 0.0 | VF |
| 'Famoso' | 0.0-4.0 | 1.5 | F | — | — | — |
| 'UC Westside' | 0.5-3.0 | 1.2 | VH | 0.5-2.5 | 0.3 | VH |
| Apr. 16, 2019 | | | | | | |
| 'Kerman' | 0.5-3.0 | 1.5 | M | 0.0-2.5 | 1.2 | M |
| 'Peters' | 0.0-2.0 | 0.8 | VF | 0.0-2.0 | 0.5 | VF |
| 'Famoso' | 0.6-3.0 | 1.5 | M | — | — | — |
| 'UC Westside' | 0.6-2.2 | 1.5 | VH | 0.0-2.0 | 0.7 | VH |
| Apr. 12, 2020 | | | | | | |
| 'Kerman' | 1.5-3.0 | 2.2 | VF | 1.0-3.0 | 2.0 | VF |
| 'Peters' | 1.5-3.5 | 1.6 | VF | 1.0-2.0 | 1.7 | VF |

TABLE 2-continued

Bloom characteristics of 4- to 7-year-old 'Kerman', 'Peters', 'Famoso', and 'UC Westside' trees at the Whisler trial, 2018-2021. Trees planted in 2014.

| | Low Elevation Plot [Z] | | | High Elevation Plot | | |
|---|---|---|---|---|---|---|
| Date evaluated | Bloom range [Y] | Mean bloom [Y] | Inflo-res-cence no. [X] | Bloom range [Y] | Mean bloom [Y] | Inflo-res-cence no. [X] |
| 'Famoso' | 1.0-6.0 | 4.0 | VH | — | — | — |
| 'UC Westside' | 0.5-2.0 | 1.4 | H | 1.0-2.0 | 1.8 | H |
| Apr. 15, 2020 | | | | | | |
| 'Kerman' | 2.6-6.0 | 4.1 | VF | 1.8-5.0 | 3.3 | VF |
| 'Peters' | 1.0-6.0 | 3.5 | VF | 0.5-6.0 | 2.9 | VF |
| 'Famoso' | 2.0-6.0 | 5.0 | VH | — | — | — |
| 'UC Westside' | 1.5-6.0 | 2.7 | H | 1.0-6.0 | 2.0 | H |
| Apr. 16, 2021 | | | | | | |
| 'Kerman' | 0.5-6.0 | 3.5 | M | 0.0-4.5 | 1.5 | M |
| 'Peters' | 0.5-6.0 | 3.5 | M | 0.0-6.0 | 1.0 | M |
| 'Famoso' | 0.0-6.0 | d | VH | — | — | — |
| 'UC Westside' | 0.2-6.0 | 3.5 | VH | 0.0-6.0 | 1.1 | H |
| Apr. 19, 2021 | | | | | | |
| 'Kerman' | 1.0-6.0 | 5.0 | M | 1.0-6.0 | 3.1 | M |
| 'Peters' | 1.0-6.0 | 4.7 | M | 0.5-6.0 | 3.0 | M |
| 'Famoso' | 6.0 | d | VH | — | — | — |
| 'UC Westside' | 1.0-6.0 | 4.8 | VH | 0.0-6.0 | 2.6 | H |

— not available

[Z] Difference above sea level between the high and low plots was approximately 100 feet.

[Y] Tree bloom ratings based on totality of individual inflorescences on the tree: 0—dormant; 1—bud push; 2—early bloom; 3—mid bloom; 4—full bloom; 5—late bloom; 6—done blooming

[X] Letters refer to estimated number of inflorescences per tree as follows:

2018 bloom ratings: VF 0-10; F 11-25; M 26-40, H 41-60; VH > 60

2019 bloom ratings: VF 0-10; F 11-25; M 26-75; H 76-100; VH > 100

2020 bloom ratings: VF 0-25; F 25-50; M 51-200; H 201-400; VH > 400

2021 bloom ratings are compared relative to one another.

[W] Each value in the table for Kerman and Peters is the mean of 5-10 trees, for 'Famoso' and 'UC Westside' it is for a single tree. Experimental trees were not replicated within each of the two plots in this trial.

TABLE 3

Bloom characteristics of 3- to 6-year-old 'Kerman', 'Peters', 'Famoso' and 'UC Westside' trees at the Corcoran trial, 2018-2021. Trees planted in 2015.

| Date evaluated | Bloom range [Z] | Mean bloom [Z] | Inflores-cence no [Y] | Relative tree size [X] |
|---|---|---|---|---|
| 2018 | | | | |
| 'Kerman' | 1.5-6.0 [W] | 5.0 | M | — |
| 'Peters' | 2.0-6.0 | 5.0 | F | — |
| 'Famoso' | 6.0 | d | M | — |
| 'UC Westside' | 1.5-6.0 | 5.0 | H | — |
| 2019 | | | | |
| 'Kerman' | — | 2.2 | — | — |
| 'Peters' | 0.5-2.5 | 1.0 | F | — |
| 'Famoso' | 1.0-6.0 | 4.5 | H | — |
| 'UC Westside' | 0.5-3.5 | 1.9 | VH | — |
| 2019 | | | | |
| 'Kerman' | — | 5.0 | | — |
| 'Peters' | — | 2.5 | F | — |
| 'Famoso' | — | d | H | — |
| 'UC Westside' | — | 4.9 | VH | — |
| 2020 | | | | |
| 'Kerman' | 1.5-3.5 | 2.0 | — | A |
| 'Peters' | 1.0-3.5 | 1.9 | M | A |
| 'Famoso' | 1.5-6.0 | 4.5 | H | A |
| 'UC Westside' | 1.0-5.0 | 2.5 | M | A |

TABLE 3-continued

Bloom characteristics of 3- to 6-year-old 'Kerman', 'Peters', 'Famoso' and 'UC Westside' trees at the Corcoran trial, 2018-2021. Trees planted in 2015.

| Date evaluated | Bloom range [Z] | Mean bloom [Z] | Inflores-cence no [Y] | Relative tree size [X] |
|---|---|---|---|---|
| 2020 | | | | |
| 'Kerman' | 1.5-6.0 | 4.6 | — | A |
| 'Peters' | 1.0-5.0 | 4.0 | M | A |
| 'Famoso' | 1.5-6.0 | 5.0 | H | A |
| 'UC Westside' | 1.0-5.0 | 4.2 | M | A |
| 2021 | | | | |
| 'Kerman' | 0.0-3.5 | 1.6 | — | — |
| 'Peters' | 0.0-3.0 | 1.5 | M | L |
| 'Famoso' | 0.0-5.0 | 2.4 | H | A |
| 'UC Westside' | 0.0-4.5 | 1.4 | H | A |
| 2021 | | | | |
| 'Kerman' | 0.5-5.0 | 4.1 | — | — |
| 'Peters' | 0.2-5.0 | 2.4 | M | L |
| 'Famoso' | 0.5-6.0 | 5.0 | H | A |
| 'UC Westside' | 0.5-6.0 | 4.1 | H | A |

[Z] Tree bloom ratings based on a visual estimate of the totality of individual inflorescences: 0 - dormant; 1 - bud push; 2 - early bloom; 3 - mid bloom; 4 - full bloom; 5 - late bloom; 6 - done blooming

[Y] Letters refer to estimated number of inflorescences per tree as follows:

2018 bloom ratings for cultivars and 'UC Westside' were compared relative to one another.

2019 bloom ratings: F < 10; M 10-25; H 26-75; VH > 75

2020 bloom ratings: F < 75; M 76 -150; H 151-250; VH > 250

2021 bloom ratings F < 150; M 151-300; H 301 - 500; VH > 500

[X] Relative to the largest trees in the trial. L is large, A is average, and S is small.

[W] Each value in the table for 'Kerman' is the average of 20 trees and the average of three trees for 'Peters', 'Famoso', and 'UC Westside'.

TABLE 4

Bloom characteristics of 3-, 4-, and 6-year-old 'Kerman', 'Peters', 'Famoso', and 'UC Westside' trees at the Westside REC trial, 2018-2019, 2021. Trees planted in 2015. Each value in the table is the mean of 2-3 trees.

| Date evaluated | Bloom range [Z] | Mean. Bloom [Z] | Inflores-cences no [Y] | Relative Tree Size [X] |
|---|---|---|---|---|
| 2018 | | | | |
| 'Kerman' [X] | — | — | none | — |
| 'Peters' | — | — | none | — |
| 'Famoso' | 0-1.0 [Z] | 0.1 [X] | F | — |
| 'UC Westside' | — | 0.0 | H | — |
| 2019 | | | | |
| 'Kerman' | 0.0-0.0 | 0.0 | M | A |
| 'Peters' | 0.0 | 0.0 | F | L |
| 'Famoso' | 0.0-0.0 | 0.0 | M | L |
| 'UC Westside' | 0.0-0.2 | 0.0 | M | A |
| 2021 | | | | |
| 'Kerman' | 3.0-6.0 | 4.0 | M | — |
| 'Peters' | 0.5-5.0 | 2.8 | F | — |
| 'Famoso' | 0.5-6.0 | 4.5 | H | — |
| 'UC Westside' | 0.3-5.0 | 2.9 | H | — |

[Z] Bloom ratings based on a visual estimate of the totality of individual inflorescences: 0 - dormant; 1 - bud push; 2 - early bloom; 3 - mid bloom; 4 - full bloom; 5 - late bloom; 6 - done blooming

[Y] Letters refer to estimated number of inflorescences per tree as follows:

Tree bloom ratings are compared relative to one another based on all entries in the trial: F = few; M = moderate; H = high; VH = very high.

[X] Relative to the largest trees in the trial. L is large, A is average, and S is small.

— Not available

TABLE 5

Summary statistics for differences in bloom synchrony, as measured by bloom-maturity ratings, among the male pollenizers ('Famoso', 'Peters', 'UC Westside') and 'Kerman' at three locations (Whisler Low, Whisler High and Corcoran) for 4 years (2018-2021).

General linear model: Transformed values [Square root (X + 0.5)] versus Location, Year and Cultivar

| Factor | Type | Levels |
|---|---|---|
| Location | Fixed | 3 |
| Year | Random | 4 |
| Cultivar | Fixed | 3 |

Analysis of Variance

| Source | DF | F value | P |
|---|---|---|---|
| Location | 2 | 0.464 | 0.448 |
| Year | 3 | 1.048 | 0.251 |
| Cultivar | 2 | 3.757 | 0.009 |
| Error | 24 | | |
| Total | 31 | | |

Differences among males from 'Kerman' in bloom-timing ratings difference test. A value closer to 0 denotes timing more coincidental with 'Kerman'. A negative number denotes that the pollinizer blooms before 'Kerman'

| Cultivar | Mean |
|---|---|
| 'Famoso' | −1.29 a[z] |
| 'Peters' | 0.58 ab |
| 'UC Westside' | 0.40 b |

[z]Values in the same column followed with different letters denote significant differences between means using Tuckey's highest significant differences test at P ≤ 0.05

[z]Values in the same column followed with different letters denote significant differences between means using Tuckey's highest significant difference test at P≤0.05

TABLE 6

Germination and quantity of pollen for the male pollenizers 'Peters', 'Famoso', and 'UC Westside' at the Whisler and Corcoran trials in Kern County Calif. during spring of 2021.

| Trial | Date pollen collected | Pollen germination, % [Z] | Pollen quantity, g·inflorescence$^{-1}$ [Z] |
|---|---|---|---|
| Whisler [Y] High elevation | | | |
| 'Peters' | 4/12 | 75.2 | 0.045 |
| 'Famoso' | — | | |
| 'UC Westside' | 4/12 | 75.5 | 0.086 |
| Low elevation | | | |
| 'Peters' | 4/12 | 12.9 | 0.036 |
| 'Famoso (1)' | 4/7 | 59.9 | 0.083 |
| 'Famoso (2)' | 4/12 | 52.1 | 0.041 |
| 'UC Westside' | 4/12 | 73.2 | 0.065 |
| Corcoran [Z] | | | |
| 'Peters' | 4/7 | 21.7 a [Y] | 0.071 a |
| 'Famoso' | 4/7 | 54.5 ab | 0.089 a |
| 'UC Westside' | 4/7 | 81.0 b | 0.177 a |

— not available

[Z] At Whisler, each value is the average for one tree in each elevation plot. At the Corcoran trial, each value is the average of three trees from a randomized, complete block experimental trial design.

[Y] Different letters in the same column denote significant differences among means at the Corcoran trial site using Fisher's protected LSD test at P ≤ 0.05.

Tree size: The 'UC Westside' tree, grafted to 'UCB-1' or 'PG1' rootstock, up to age seven in the current trials, is similar in trunk size to 'Famoso' and 'Peters'. Trunk scion diameter comparisons among 'UC Westside', 'Peters' and 'Famoso' were taken on Jun. 28, 2023. Scion diameter was measured 150 mm above the graft union on these now 8-year-old trees. These measurements and statistical analysis are shown in Table 7. There were no significant differences on trunk scion diameter among 'UC Westside', 'Peters', and 'Famoso' based on the limited sample size at the Corcoran Trial. Tree height is a function of pruning methodology and training activities which are practiced intensively during the first three years of growth.

TABLE 7

| Cultivar | Trunk Scion Diameter, mm* |
|---|---|
| 'UC Westside' | 73 a |
| 'Peters' | 76 a |
| 'Famoso' | 83 a |

*Values in the same column followed by different letters are significantly different by Fisher's protected least significant difference test a P ≤ 0.05.

Figure 2:
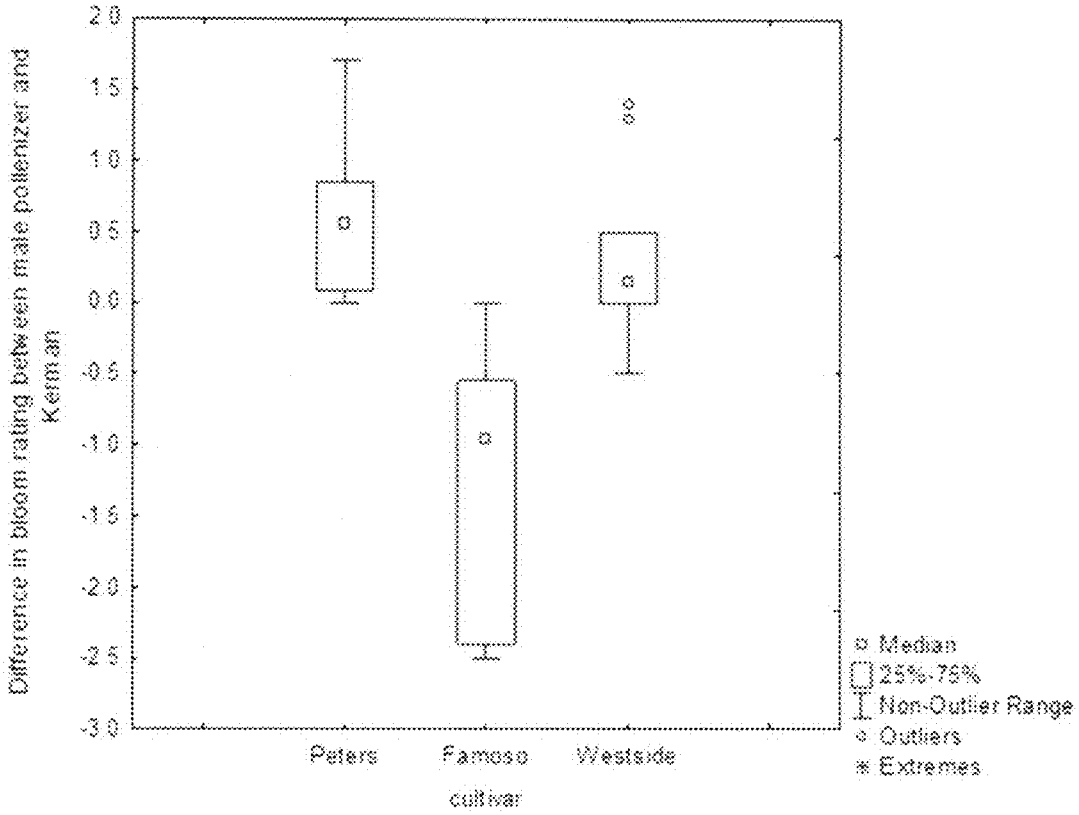
FIG. 2 is a graph depicting the differences in bloom rating between the individual male cultivars and 'Kerman' averaged over three trial locations from 2018 through 2021. The bloom rating scale has a range of 0 through 6. The closer the value of the difference between a pollinizer and 'Kerman' is to 0, the better the bloom synchrony. A negative number denotes the cultivar blooms before 'Kerman'.

'UC Westside' branch length tends to be somewhat shorter than 'Peters' as the trees move from juvenility to early flowering (FIG. 1). The reason for the shorter branch length is not clear and may be due to parentage or to the shorter juvenility period and profuse flowering that characterizes 'UC Westside' and 'Famoso' in their early development years (FIGS. 1 and 2).

Leaves: Leaves are simple compound imparipinnate with 1 to 2 pairs of oppositely arranged leaflets. Leaf, petiole, and leaflet sizes and shapes are similar for 'UC Westside', 'Famoso', and 'Peters'. 'Peters' leaves are slightly larger. 'UC Westside' leaves are 11 cm to 15 cm long with 3 cm to 8 cm leaflets. Leaves can vary considerably in shape, depending on their developmental stage and position on shoots (e.g., more lateral vs. more terminal), in general being ovate with cuspidate to rounded tips and rounded base. Margins of leaf blades are entire. Leaf surfaces are glabrous, smooth and waxy. Leaves range from light green at first emergence to dark green at maturity. Leaf, leaflet, and petiole size measurements are shown in Table 7.

TABLE 7

| Cultivar | Petiole Length (cm) | Leaf Length (cm) | Leaf Width (cm) | Leaflet Length (cm) | Leaflet Width (cm) |
|---|---|---|---|---|---|
| 'UC Westside' | 3 | 13.2 | 11.8 | 6 | 4.8 |
| 'Peters' | 3.8 | 16.0 | 15.9 | 7.5 | 4.8 |
| 'Tejon' | 3.3 | 16.8 | 15.0 | 6.8 | 4.2 |
| 'Famoso' | 2 | 12.4 | 14.4 | 6.5 | 4.9 |
| 'Randy' | 2.8 | 13.5 | 13.2 | 7.3 | 5.2 |

Color evaluations were done on at least 3 leaves, each new and mature, collected at random from 'UC Westside', 'Peters', 'Tejon', 'Famoso', and 'Randy'. Leaf colors are also similar for leaves of all the cultivars. Color values are provided in Table 8. Numbers provide subtle differences in the observed color. Bottom leaf surfaces are usually 1-2 shades lighter than the top.

TABLE 8

| Cultivar | Type | Color |
|---|---|---|
| 'UC Westside' | Petiole | 160A, 145B |
| | Top Leaf | 148A |
| | Bottom Leaf | 148A, 147B |
| 'Peters' | Petiole | 160A, 145BC |
| | Top Leaf | 146A, 147B |
| | Bottom Leaf | 148A |
| 'Tejon' | Petiole | 160B, 145BC |
| | Top Leaf | 148A, 147A |
| | Bottom Leaf | 148A, 146B |
| 'Famoso' | Petiole | 160A, 145B |
| | Top Leaf | 147A |
| | Bottom Leaf | 148A, 147B |
| 'Randy' | Petiole | 160BC, 145BC |
| | Top Leaf | 147A |
| | Bottom Leaf | 148A, 147B, 147A |

Figure 3:
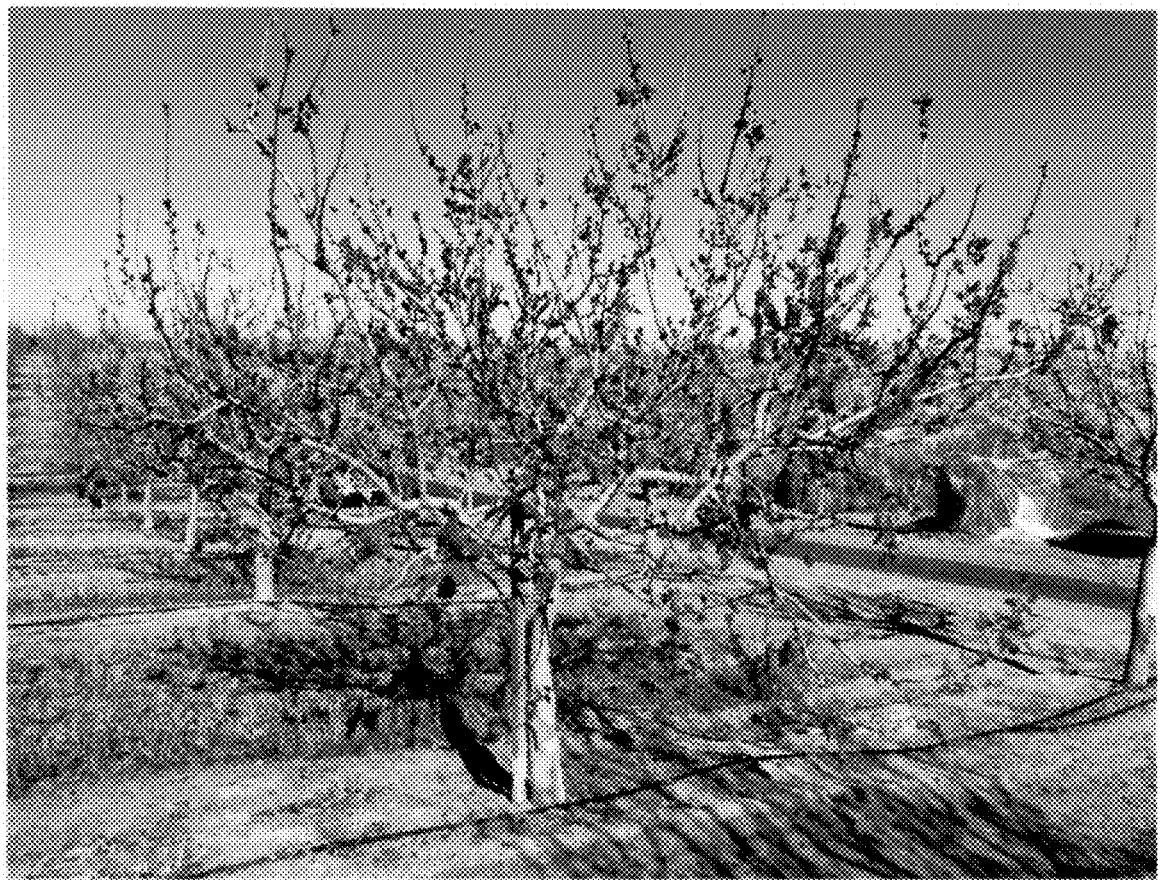
FIG. 3 is a photograph of a 7-year-old 'UC Westside' tree in the high elevation plot in early bloom in April 2021 at the Whisler trial in Kern County. The tree was grafted to 'PG1' rootstock in 2014 and shows tree size and a large number of inflorescences.
Figure 4:
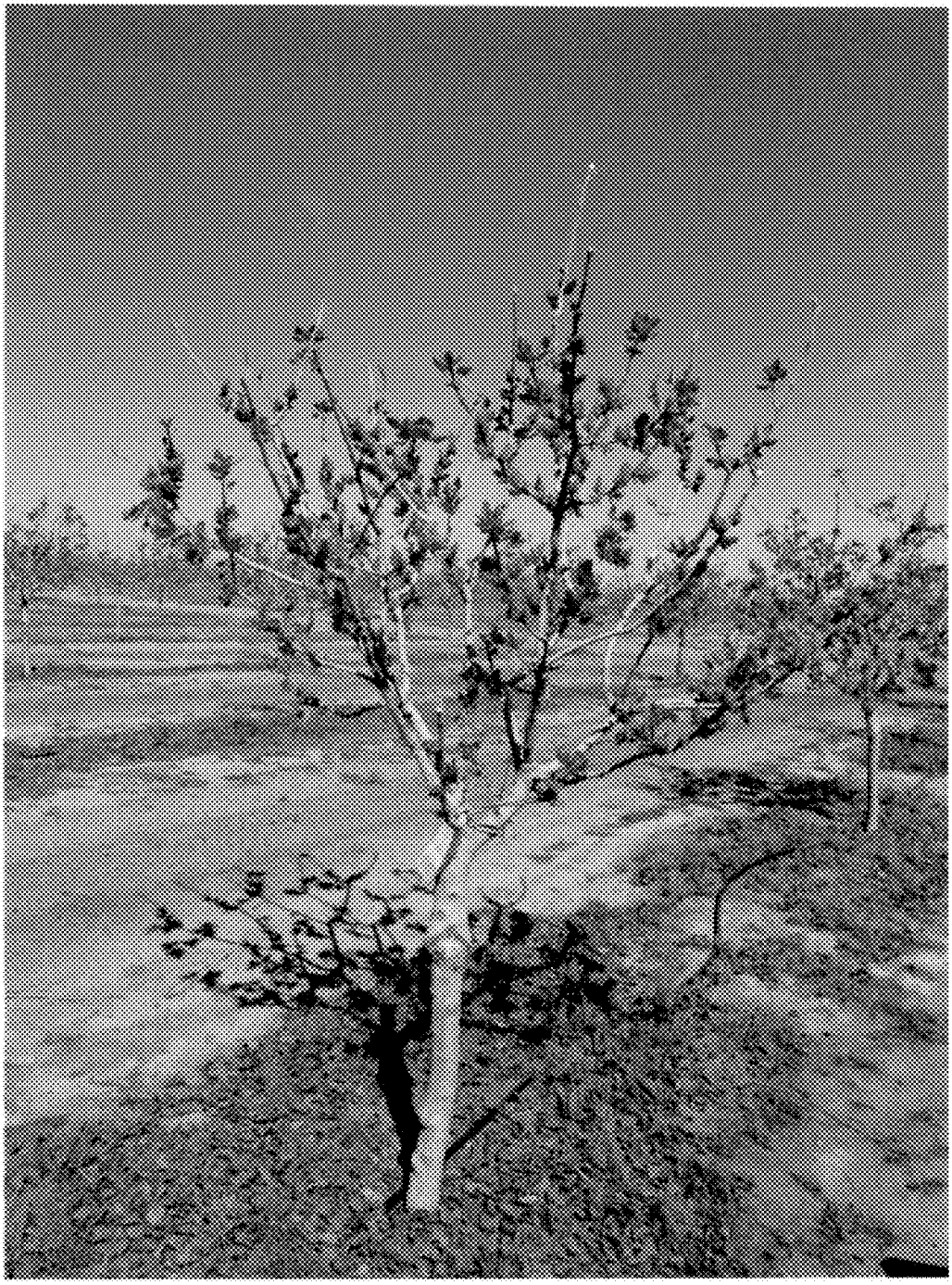
FIG. 4 is a photograph of a 6-year-old 'UC Westside' tree in the Corcoran trial slightly passed full bloom in April 2021. There is a range of open and unopened flowers. The tree was grafted to 'UCB-1' clonal rootstock in 2015. Trees in the background are 'Kerman'.
Figure 5:
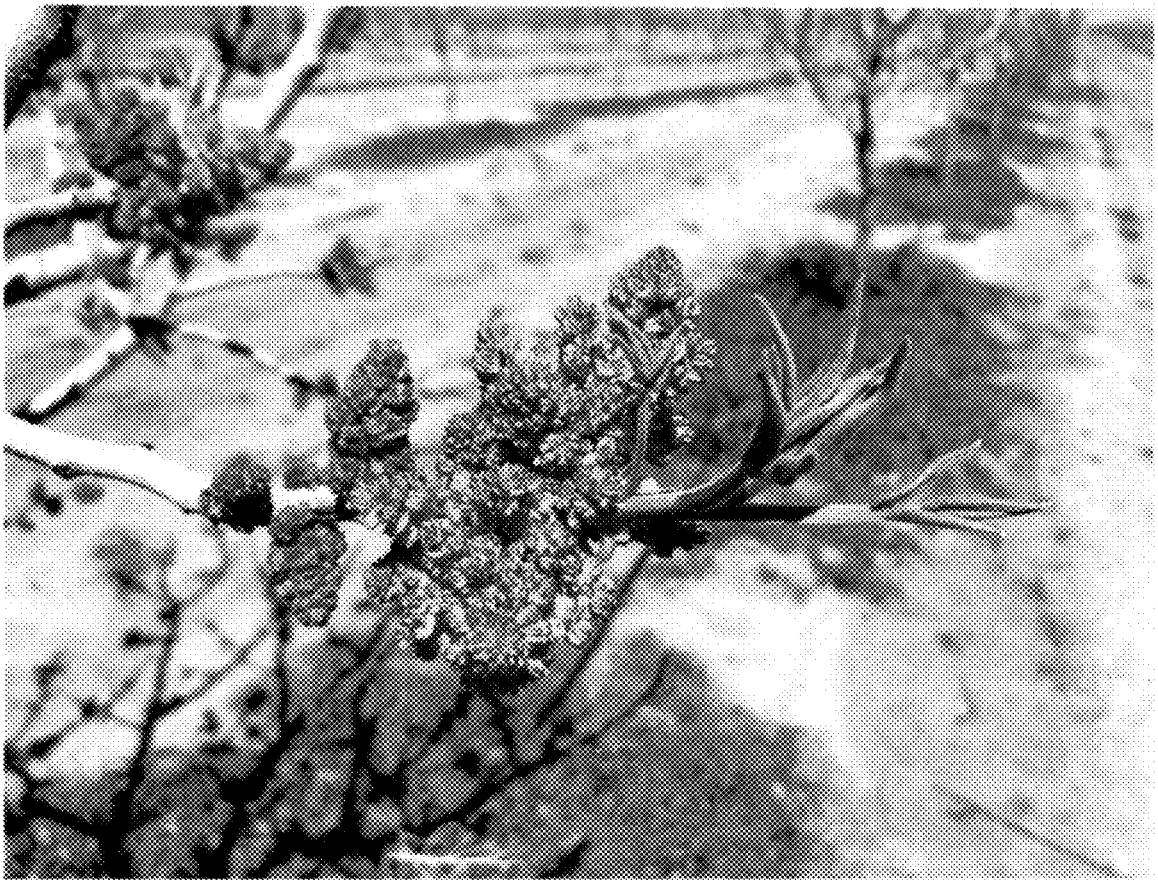
FIG. 5 is a photograph of inflorescences of a 6-year-old 'UC Westside' tree in April 2021 early in the bloom period.
Figure 6:
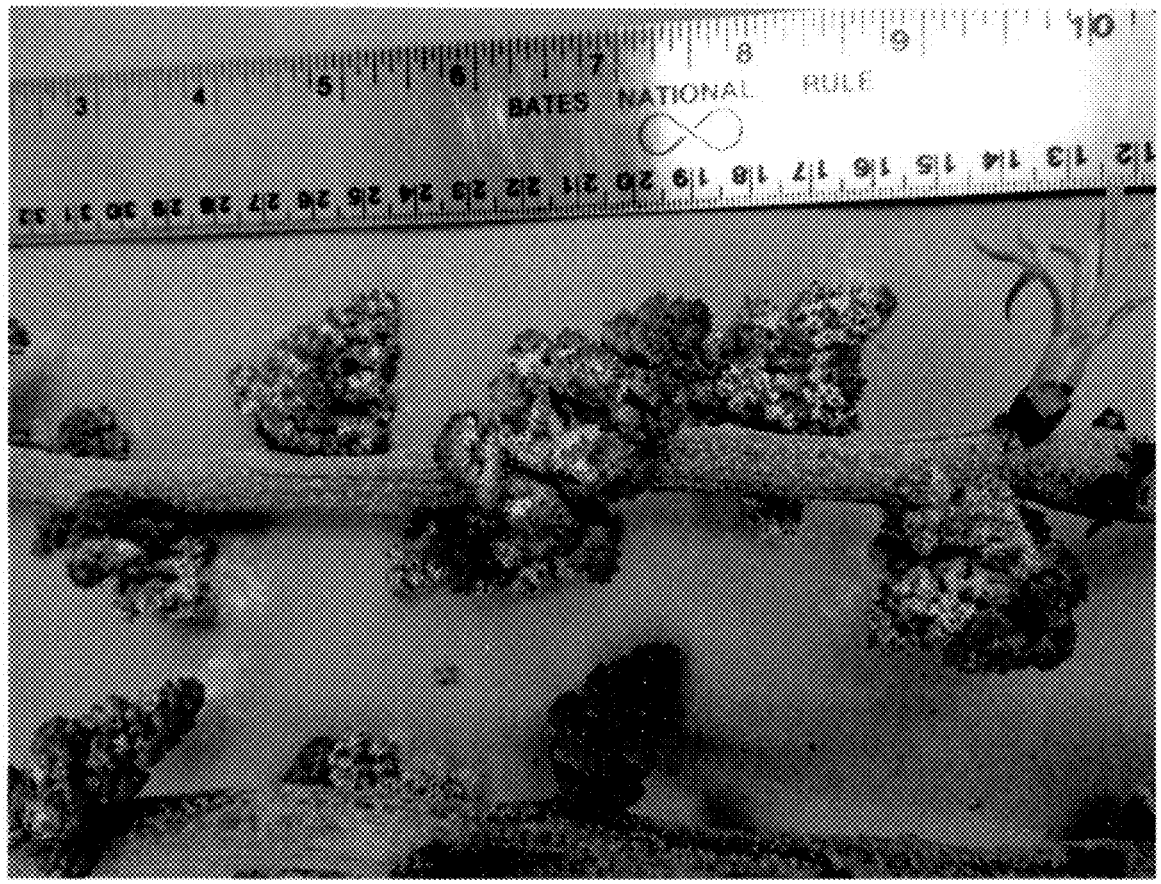
FIG. 6 is a photograph of dehiscing pollen from 'UC Westside' inflorescences collected in April 2021 in the Corcoran trial.

Inflorescences: Female inflorescences are born laterally alternately on branches, rarely as terminal buds. They are located on one year old wood. The 'UC Westside' inflorescences are similar in size and color to 'Peters' and 'Famoso' male pistachios (FIGS. 3 and 4). The flower buds form a branched compound inflorescence of the panicle form. Individual flowers are 0.5 mm to 1 mm in size. All flowers are male. Flowers do not have petals. The panicles are 3 to 7 cm long with considerable variation in size. Flower development is from base to tip of the panicle and typically spans a 3-week period, depending on weather conditions during individual seasons. Panicles are yellow as is the pollen. Tips of the panicles are tinged red prior to opening of individual flowers.

Plant Winter Hardiness, Heat Tolerance, and Drought Tolerance: 'UC Westside', as is typical of *Pistacia vera* L., will tolerate temperatures greater than −5° C. to −10° C. The rootstock on which it is grafted, however, can sustain significant damage at −5° C. after a few hours. The 'UC Westside' cultivar is typically grown in a hot dry environment, and has been grown in a location having typical summer temperatures greater than 40° C. to 42° C. All California pistachio cultivars are grown as an irrigated crop and require about 1000 mm of water during the growing season. Pistachio cultivars will tolerate poor-quality water and do not show significant yield loss or damage up to EC (electrical conductivity) 8-12.

Response to Pests and/or Diseases: 'UC Westside' has not been specifically evaluated for resistance or susceptibility to pistachio diseases. This variety is grown in a location where typical pistachio diseases are minimal and which is managed to minimize disease development. It is expected that susceptibility to *Botryosphaeria dothidea, Botrytis cinerea*, or *Alternaria alternata* would be similar to other commercial pistachio cultivars since *Pistacia vera* L. in California is generally susceptible to these diseases. Most pistachio insect pests are controlled with insecticides, which have been used where 'UC Westside' is grown. Significant differences in unspecified insect damage were not found among the tested cultivars, including 'UC Westside'.

Application and Use

'UC Westside' male pistachio can provide more complete pollination for 'Kerman' in the Central Valley of California than is provided by the standard 'Peters' male. 'UC Westside' has a reduced juvenility period compared to 'Peters' often producing inflorescences in Year 3 and a dense bloom in Years 4 and 5, unlike 'Peters', which may take five years to begin producing flowers. The flowering period of 'UC Westside' has been coincident with 'Kerman' in years with moderate to high chill and has produced a dense bloom in years of low chill, which overlaps the later bloom period of 'Kerman'.

'Peters' flowering overlap with 'Kerman' was exceptionally poor in the low chill crop years of 2014 and 2015. Therefore, 'Famoso' was released as a pollenizer for 'Kerman' in 2018. Previous research has demonstrated that 'Famoso' bloom is highly synchronous with 'Peters' in low chill years and, like 'UC Westside', has a reduced juvenility period compared to 'Peters' and produces flowers three to four years after budding. However, in high-chill years, the bloom period of 'Famoso' may be too early to fully cover the latest bloom of 'Kerman'. Without having a suitable replacement for 'Peters' under high chill conditions, it is recommended that growers in the Central Valley plant a 50-50 mix of 'Famoso' and 'Peters' trees as pollenizers for 'Kerman'. With the advent of 'UC Westside', 'UC Westside' can replace 'Peters' in the 50-50 mix. 'Famoso' and 'UC Westside', together, will provide a higher quantity of pollen and better bloom synchrony during 'Kerman' bloom than the currently recommended combination of 'Peters' and 'Famoso', as the trees move from juvenility to maturity and under all foreseeable winter chilling scenarios in the Central Valley of California. In addition, 'UC Westside' would prove useful if an improved late-blooming female cultivar were released in the future.

We claim:

1. A new and distinct variety of pistachio tree designated 'UC Westside' substantially as described and illustrated herein.

* * * * *